(12) United States Patent
Burton

(10) Patent No.: US 7,311,106 B1
(45) Date of Patent: Dec. 25, 2007

(54) NIPPLE SELECTION APPARATUS AND METHOD

(76) Inventor: Julie McCulloch Burton, 1309 Woodstock Way #301, Bellingham, WA (US) 98226

( * ) Notice: Subject to any disclaimer, the term of this patent is extended or adjusted under 35 U.S.C. 154(b) by 318 days.

(21) Appl. No.: 11/119,162

(22) Filed: May 2, 2005

(51) Int. Cl.
*A61B 19/00* (2006.01)

(52) U.S. Cl. ......................................... 128/898; 604/74

(58) Field of Classification Search .................. 604/74, 604/68, 78; 128/898
See application file for complete search history.

(56) References Cited

U.S. PATENT DOCUMENTS

| | | |
|---|---|---|
| 2,208,089 A | 7/1940 | Von Grolman |
| 2,542,505 A | 2/1951 | Gascoigne |
| 3,822,703 A | 7/1974 | Davisson |
| 4,740,196 A | 4/1988 | Powell |
| D309,500 S | 7/1990 | Yuan et al. |
| D313,103 S | 12/1990 | Kawano |
| 5,049,126 A | 9/1991 | Larson |
| 5,108,686 A | 4/1992 | Griffin |
| 5,843,029 A | 12/1998 | Bachman et al. |
| D404,825 S | 1/1999 | Reed |
| 6,109,100 A * | 8/2000 | Buckley et al. ............... 73/198 |

* cited by examiner

*Primary Examiner*—Nicholas Lucchesi
*Assistant Examiner*—Theodore J Stigell

(57) ABSTRACT

A nipple selection apparatus includes a breast pump that includes a breast receiving housing, a suction device in fluid connection with the housing and a pressure gauge that is in fluid connection with the housing and is adapted for measuring the pressure within the housing. The gauge provides a relative measurement of the force required to extract milk from a mother's breast. A nipple for a bottle may then be selected that has a flow rate corresponding to the relative measurement.

2 Claims, 4 Drawing Sheets

NIPPLE SELECTION APPARATUS AND METHOD

BACKGROUND OF THE INVENTION

1. Field of the Invention

The present invention relates to breast pump and nipple devices and more particularly pertains to a new breast pump and nipple device for aiding a mother in determining the relative negative pressure, or suction force, required to extract milk from a breast in order to select a bottle nipple having a flow rate corresponding to that negative pressure.

2. Description of the Prior Art

The use of breast pump and nipple devices is known in the prior art. U.S. Pat. No. 2,542,505 describes a device for stimulating a breast for removing breast milk therefrom. Another type of breast pump and nipple device is U.S. Pat. No. 5,049,126 having a suction device and a plurality of nipple stimulations inserts for increasing flow of milk from a breast. A nipple device is found in U.S. Pat. No. 5,108,686 and includes a device and method adapted for replicating a human nipple for use during nursing. A generally conventional breast pump assembly is found in U.S. Pat. Design No. 313,103.

While these devices fulfill their respective, particular objectives and requirements, the need remains for a device that not only is capable of pumping breast milk from a mother, but is also able to measure the relative suction, or pressure, required to suction the milk out of the breast. Once that measurement has been determined, a nipple may be chosen that has a flow rate corresponding to that measurement so that an infant will be more comfortable with drinking from a bottle.

SUMMARY OF THE INVENTION

The present invention meets the needs presented above by generally comprising a breast pump that includes a breast receiving housing, a suction device in fluid connection with the housing and a pressure gauge that is in fluid connection with the housing and is adapted for measuring the pressure within the housing. The gauge provides a relative measurement of the force required to extract milk from a mother's breast. A nipple for a bottle may then be selected that has a flow rate corresponding to the relative measurement.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
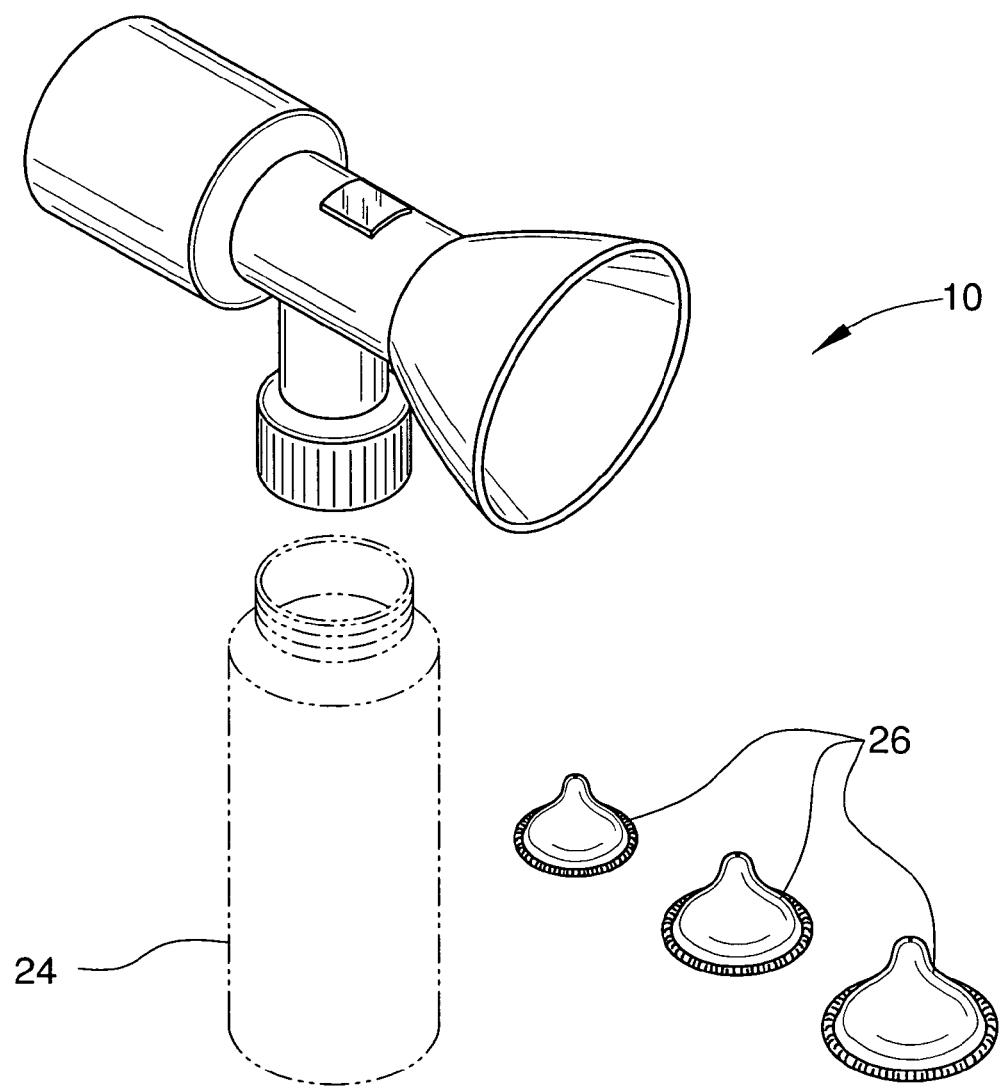
FIG. 1 is a perspective view of a nipple selection apparatus and method according to the present invention.
Figure 2:
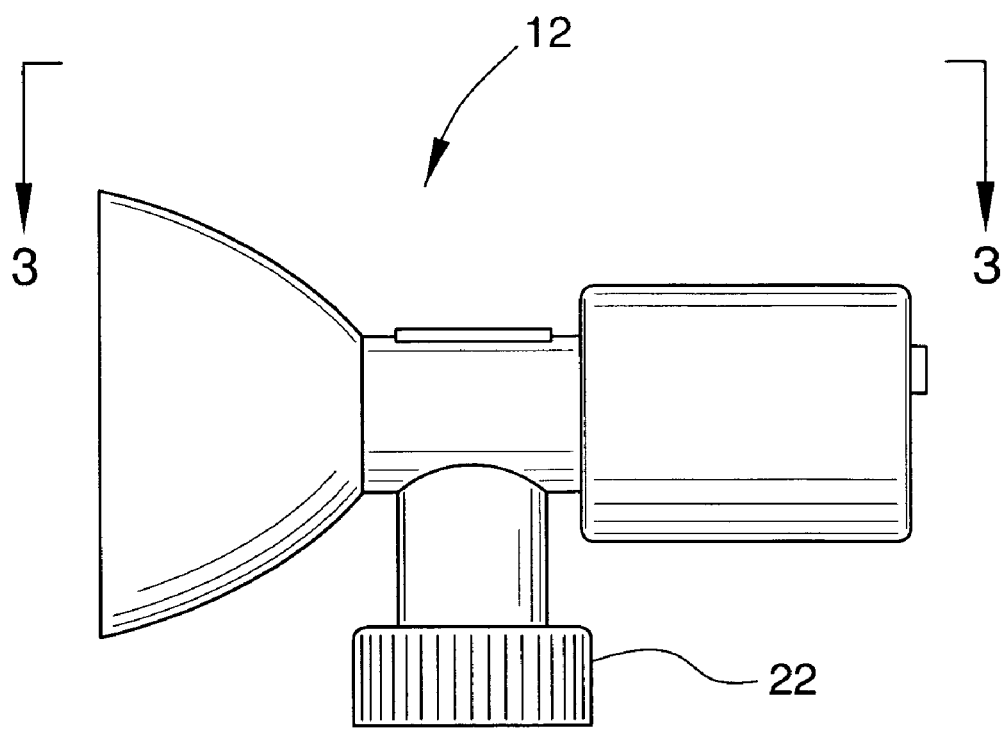
FIG. 2 is a side view of the present invention.
Figure 3:
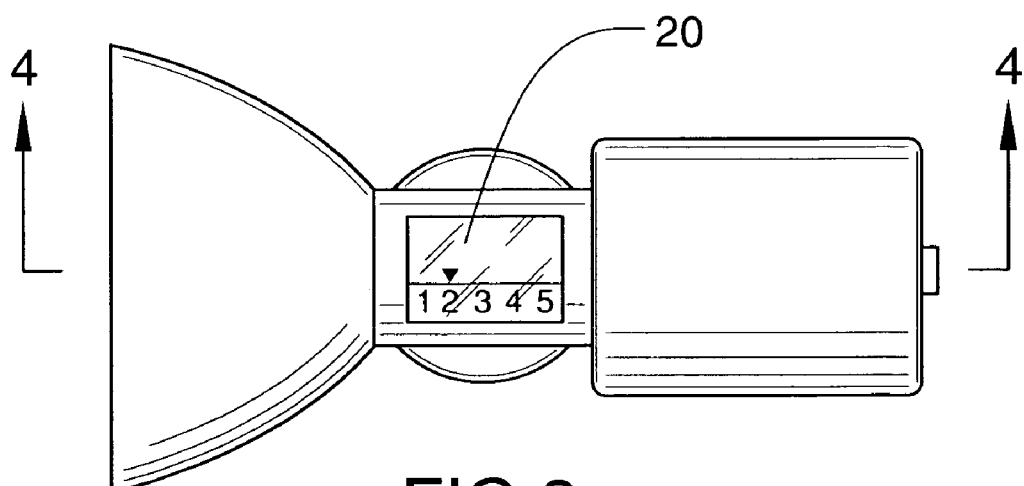
FIG. 3 is a top view taken along line 3-3 of FIG. 2 of the present invention.
Figure 4:
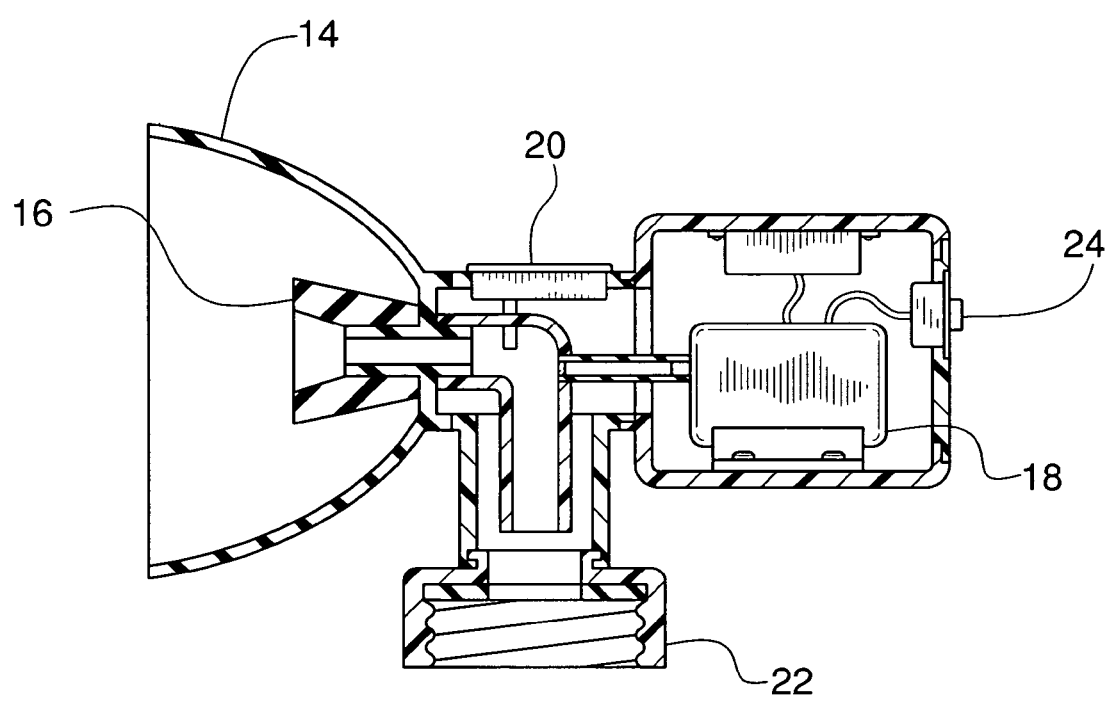
FIG. 4 is a cross-sectional view taken along line 4-4 of FIG. 3 of the present invention.
Figure 5:
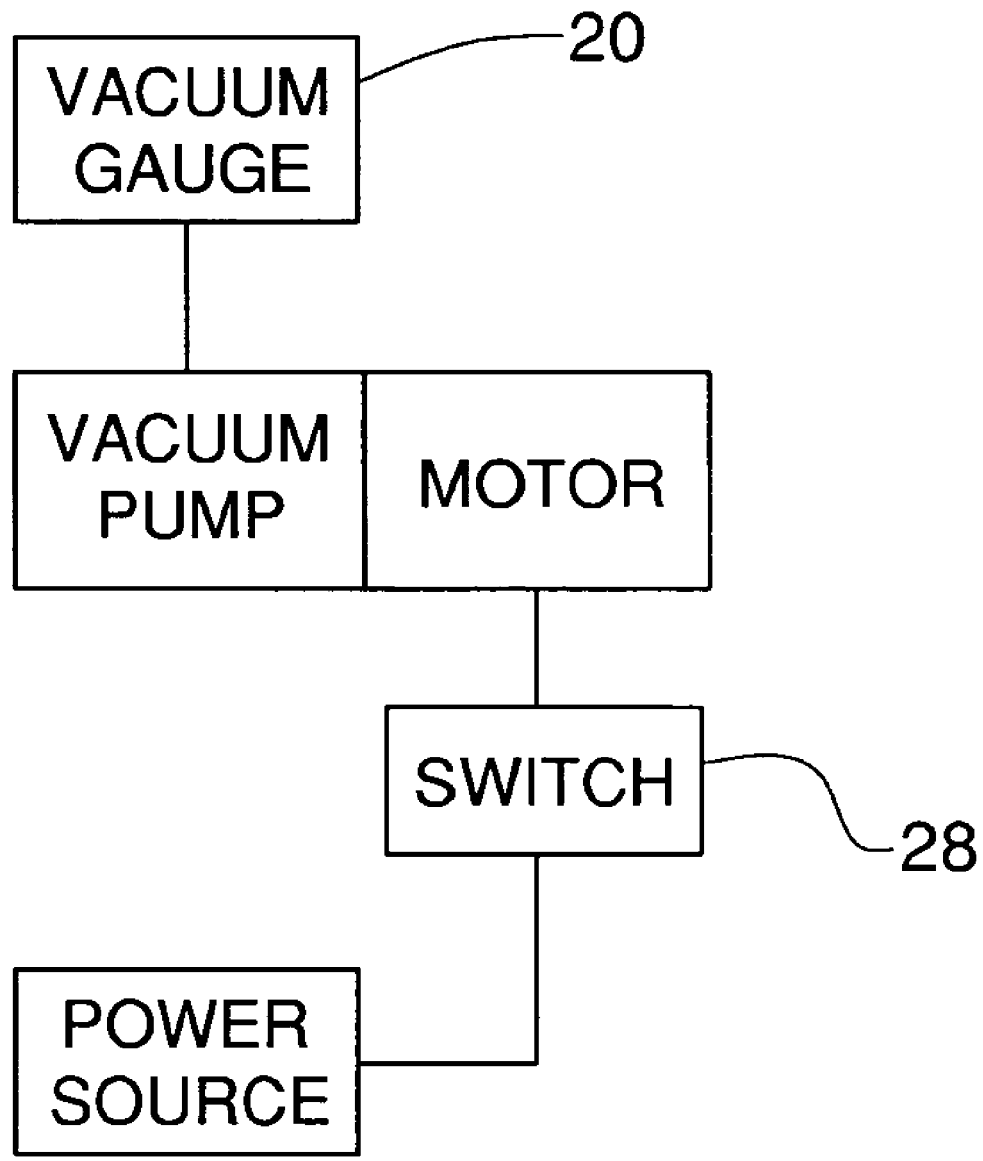
FIG. 5 is a schematic view of the present invention.

With reference now to the drawings, and in particular to FIGS. 1 through 5 thereof, a new breast pump and nipple device embodying the principles and concepts of the present invention and generally designated by the reference numeral 10 will be described.

As best illustrated in FIGS. 1 through 5, the nipple selection apparatus and method 10 generally comprises providing a breast pump 12 that includes a breast receiving housing 14 that may include a nipple-engaging funnel 16. A suction device 18 is in fluid connection with the housing 14. A pressure gauge 20 is in fluid connection with the housing 14 and is adapted for measuring the pressure within the housing 14. The gauge 20 provides a relative measurement. A relative measurement is used because while an exact pressure reading may be used, it is preferred that a scale be implemented, such as a scale of 1 to 5 for easy reading by a layperson. An outlet 22 is fluidly coupled to the housing 14 and a bottle 24 is removably coupled to the outlet 22. An on/off switch 28 is electrically coupled to the suction device 18.

A plurality of nipples 26 is provided. Each of the nipples 26 is removably positionable on a bottle 24 and each of the nipples 26 has a variable flow rate at a constant pressure. The pressure to be used will be equal to the suction of a typical infant and may be determined at different ages so that nipples 26 may be provided for different aged infants as well. The flow rate may be altered by either varying the elasticity and resilience of the nipples 26 or by altering the size of the openings in the nipples 26. Each of the nipples 26 has a rating corresponding to the flow rate so that each of the nipples 26 has a different rating. Each of the ratings corresponds to a different relative measurement. Thus, a reading of 1 on the gauge 20 will correspond to a number 1 rated nipple 26. A nipple 26 is then selected that has a rating corresponding to the relative measurement when milk is extracted from a breast, and thereby a selected nipple defined. The selected nipple 26 is then positioned on a bottle 24 in a conventional manner and given to an infant. As the flow rate through the nipple 26 should be comparable to the flow rate when the infant breastfeeds, the infant will not be easily confused and fussy when switching between direct breastfeeding and bottle-feeding.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of providing a proper nipple for a bottle, said method comprising the steps of:
    providing a breast pump including;
        a breast receiving housing;
        a suction device being in fluid connection with said housing;
        a pressure gauge being in fluid connection with said housing and being adapted for measuring the pressure within said housing, said gauge providing a relative measurement during extraction of breast milk;
    providing a plurality of nipples, each of said nipples being removably positionable on a bottle, each of said nipples having a variable flow rate at a constant pressure, each of said nipples having a rating corresponding to said flow rate such that each of said nipples has a different rating, each of said ratings corresponding to a different relative measurement;
    extracting breast milk with said breast pump and reading said relative measurement;
    selecting a nipple having a rating corresponding to said relative measurement to define a selected nipple; and
    positioning said selected nipple on a bottle.

2. A method of providing a proper nipple for a bottle, said method comprising the steps of:
    providing a breast pump including;
        a breast receiving housing;
        a suction device being in fluid connection with said housing;
        a pressure gauge being in fluid connection with said housing and being adapted for measuring the pressure within said housing, said gauge providing a relative measurement during extraction of breast milk;
        an outlet being fluidly coupled to said housing;
        a bottle being removably coupled to said outlet;
    providing a plurality of nipples, each of said nipples being removably positionable on a bottle, each of said nipples having a variable flow rate at a constant pressure, each of said nipples having a rating corresponding to said flow rate such that each of said nipples has a different rating, each of said ratings corresponding to a different relative measurement;
    extracting breast milk with said breast pump and reading said relative measurement;
    selecting a nipple having a rating corresponding to said relative measurement to define a selected nipple; and
    positioning said selected nipple on a bottle.

* * * * *